US010139322B2

(12) United States Patent
Olivier et al.

(10) Patent No.: US 10,139,322 B2
(45) Date of Patent: Nov. 27, 2018

(54) SAMPLE PREPARATION DEVICE

(71) Applicant: Merck Patent GmbH, Darmstadt (DE)

(72) Inventors: Stephane Olivier, Rosheim (FR); Pierre Guedon, Rosheim (FR); Florian Allard, Strasbourg (FR)

(73) Assignee: MERCK PATENT GMBH, Darmstadt (DE)

( * ) Notice: Subject to any disclaimer, the term of this patent is extended or adjusted under 35 U.S.C. 154(b) by 850 days.

(21) Appl. No.: 14/412,869

(22) PCT Filed: Jun. 14, 2013

(86) PCT No.: PCT/EP2013/001770
§ 371 (c)(1),
(2) Date: Jan. 5, 2015

(87) PCT Pub. No.: WO2014/005669
PCT Pub. Date: Jan. 9, 2014

(65) Prior Publication Data
US 2015/0153257 A1 Jun. 4, 2015

(30) Foreign Application Priority Data

Jul. 3, 2012 (EP) .................................... 12290219

(51) Int. Cl.
*G01N 1/40* (2006.01)
*B01L 3/00* (2006.01)
(Continued)

(52) U.S. Cl.
CPC ......... *G01N 1/4077* (2013.01); *B01D 63/087* (2013.01); *B01D 69/10* (2013.01);
(Continued)

(58) Field of Classification Search
CPC ...... B01D 35/30; B01D 63/087; B01D 69/10; C12M 29/04; C12M 33/14;
(Continued)

(56) References Cited

U.S. PATENT DOCUMENTS 4,036,698 A 7/1977 Bush et al.
4,070,249 A 1/1978 Janin et al.
(Continued)

FOREIGN PATENT DOCUMENTS

CN 202237447 U 5/2012
DE 3012085 A1 10/1981
(Continued)

OTHER PUBLICATIONS

Office Action in corresponding JP Appln. No. 2015-518882 dated Apr. 6, 2017.
(Continued)

*Primary Examiner* — Lyle Alexander
*Assistant Examiner* — Bryan Kilpatrick
(74) *Attorney, Agent, or Firm* — Millen White Zelano and Branigan, PC; Csaba Henter

(57) ABSTRACT

A sample preparation device, preferably for sterility testing, comprising a manifold including one or more receptacles for filtration units and at least one inlet and/or outlet port. The receptacle(s) is/are respectively provided with one or more connectors for establishing a fluid connection with mating ports of the filtration units and media containers/vials upon insertion of the same into the respective receptacles. The connectors are in fluid communication with the inlet and outlet port(s) via channels defined in the manifold to allow a desired fluid transfer through the manifold.

20 Claims, 8 Drawing Sheets

(51) Int. Cl.
*C12M 1/12* (2006.01)
*B01D 69/10* (2006.01)
*B01D 63/08* (2006.01)
B01D 35/30 (2006.01)
C12M 1/00 (2006.01)
C12M 1/26 (2006.01)
G01N 35/10 (2006.01)
G01N 35/00 (2006.01)

(52) U.S. Cl.
CPC ............... *B01L 3/502* (2013.01); *B01L 3/563* (2013.01); *C12M 37/06* (2013.01); *B01D 2313/04* (2013.01); *B01L 2200/026* (2013.01); *B01L 2200/04* (2013.01); *B01L 2200/0689* (2013.01); *B01L 2200/141* (2013.01); *B01L 2300/044* (2013.01); *B01L 2300/0672* (2013.01); *B01L 2300/0681* (2013.01); *B01L 2300/0803* (2013.01); *B01L 2300/0809* (2013.01); *G01N 2001/4088* (2013.01)

(58) Field of Classification Search
CPC .............. B29L 2031/14; G01N 1/4077; G01N 1/4005; G01N 2001/4088; G01N 35/10; G01N 2035/00475; B01L 2200/026; B01L 2300/0681; B01L 3/502
USPC ......... 422/534, 501, 504; 73/863.23; 141/21
See application file for complete search history.

(56) References Cited

U.S. PATENT DOCUMENTS

| | | | |
|---|---|---|---|
| 5,137,031 A * | 8/1992 | Guirguis | A61B 10/0045 600/575 |
| 5,288,638 A | 2/1994 | Lemonnier | |
| 5,957,898 A | 9/1999 | Jepson et al. | |
| 7,468,163 B2 | 12/2008 | Clauss | |
| 7,806,274 B2 | 10/2010 | Scott et al. | |
| 7,943,372 B2 | 5/2011 | Olivier | |
| 9,493,815 B2 | 11/2016 | Cooney et al. | |
| 2003/0008388 A1 | 1/2003 | Barbera-Guillem | |
| 2004/0188344 A1 | 9/2004 | Scott et al. | |
| 2005/0233436 A1 | 10/2005 | Clauss | |
| 2006/0163125 A1 * | 7/2006 | Olivier | G01N 1/4005 210/86 |
| 2008/0090285 A1 | 4/2008 | Olivier | |
| 2010/0279417 A1 | 11/2010 | Clay | |

FOREIGN PATENT DOCUMENTS

| | | |
|---|---|---|
| DE | 60029623 T2 | 7/2007 |
| EP | 1862532 A1 | 12/2007 |
| JP | 6141890 A | 5/1994 |
| JP | 2008295458 A | 12/2008 |
| JP | 2009510472 A | 3/2009 |
| WO | 90/02169 A1 | 3/1990 |
| WO | 2004037380 A1 | 5/2004 |
| WO | 2004071629 A1 | 8/2004 |
| WO | 2011034620 A2 | 3/2011 |

OTHER PUBLICATIONS

English language machine translation of DE3012085A1 dated Oct. 22, 1981 to Sartorius GMBH.
International Search Report from PCT Application No. PCT/EP2013/001770 dated Dec. 9, 2013.
English translation Abstract of CN202237447U published May 30, 2012 (1 page).

* cited by examiner

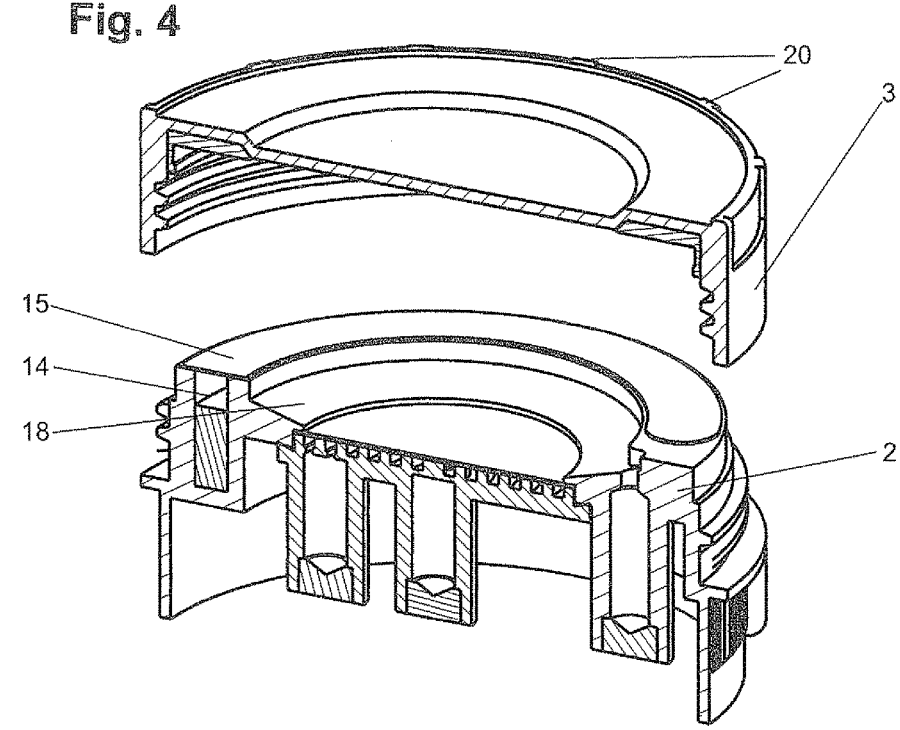
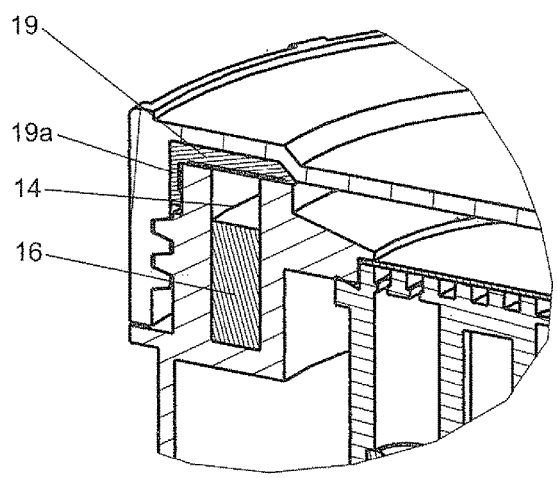
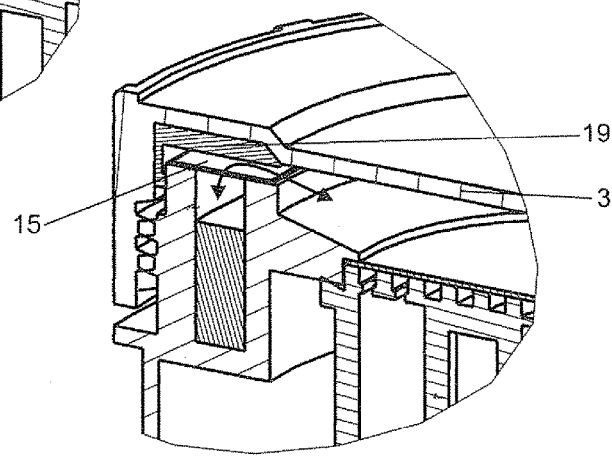

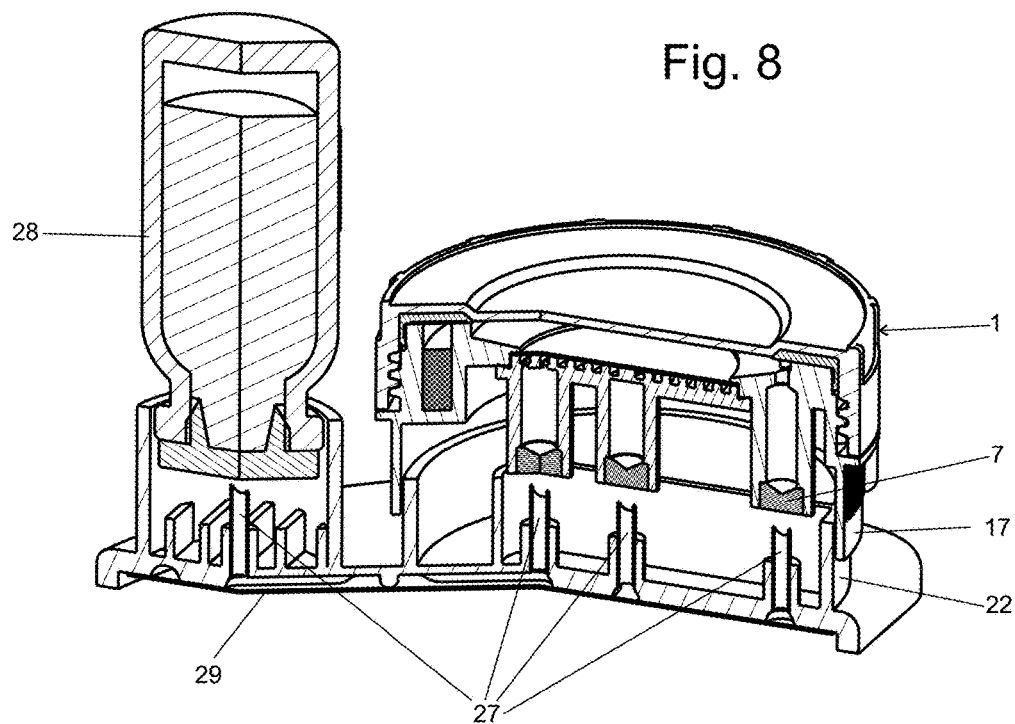
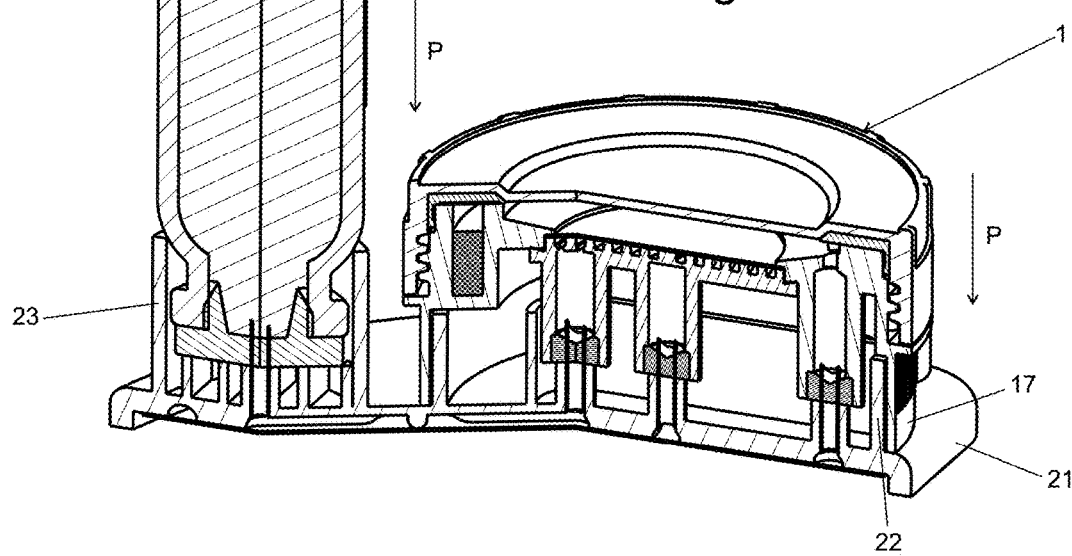

Fig. 13B
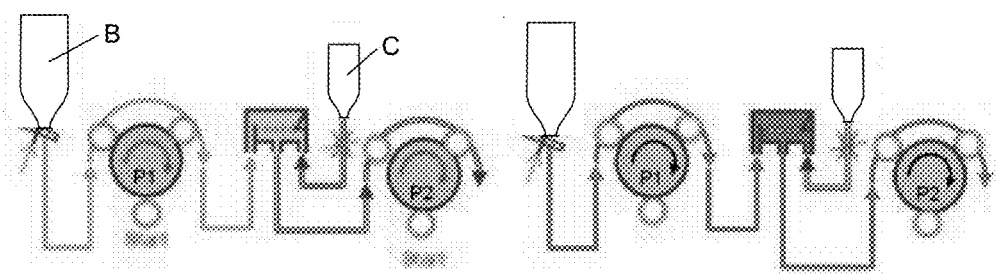
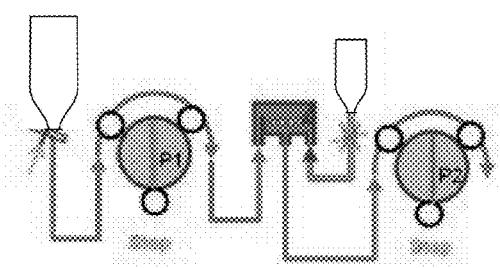
Fig. 13C
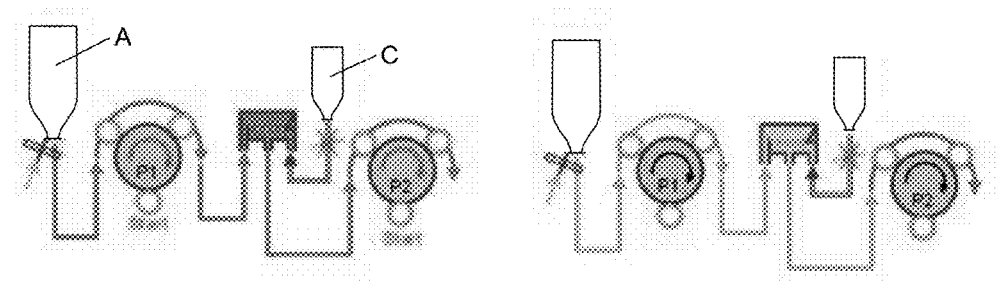
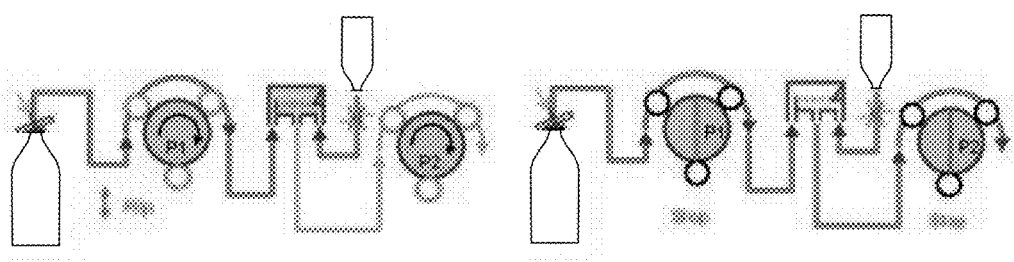

SAMPLE PREPARATION DEVICE

The present invention relates to a filtration unit for a sample preparation device and to a sample preparation device, both preferably for sterility or bioburden testing. A previous method and an apparatus for sterility testing of solutions, such as antibiotic solutions to determine the presence of microorganisms, is described in U.S. Pat. No. 4,036,698. The apparatus comprises a canister formed as a cylinder of transparent material provided with two ports at one end and each provided with removable sealing caps. One of the ports includes a hydrophobic microporous filter which is supported by a support member. A base member in which a third port is located which is also provided with a removable sealing cap closes an opposite end of the canister. In the method of sterility testing using this apparatus the solution to be tested is flowed through the cylinder having a microporous membrane filter which strains microorganisms from the solution and concentrates them on the microporous filter. Thereafter the cylinder is flushed with a sterile solution, followed by filling the cylinder with an appropriate growth culture medium with the filter being vented, during this step, through a vent having a hydrophobic filter to prevent intake of bacteria. The presence of microorganisms in the original solution to be tested is determined by visual observation of the turbidity of the growth solution after an appropriate incubation period at suitable temperature. Where more than one microorganism is being tested for, aliquots of the test solution are flowed into identical plastic cylinders. The cylinders are intended to be disposables constructed economically enough to be thrown away after each test.

This apparatus and associated method has disadvantages in that the set-up of the system is relatively complex since it requires the external separate connection of numerous components (containers, pumps, valves etc.) via plural segments of tubing. Furthermore, due to the various manual set-up steps the risk of handling mistakes is high and the portion of manual work and thus labor cost is considerable. If all the elements of the system have to be discarded after use, the volume and mass of waste is high which is increasingly problematic under ecological and economical considerations. This system cannot be automated and the apparatus in the form of the canister is bulky and unpractical to handle, especially during incubation and subsequent identification.

Further solutions for some of the above aspects are known in the art but none of these systems has achieved a satisfactory level of efficiency and automation yet.

It is the object of the invention to provide a further improved filtration unit for a sample preparation device and a sample preparation device, preferably for sterility or bioburden testing.

The invention accordingly provides, preferably for sterility testing, a filtration unit as defined in claim 1, a sample preparation device as defined in claim 10, and a sample preparation system as defined in claim 17. Preferred embodiments of the filtration unit and of the sample preparation device are defined in the dependent claims.

The present invention specifically provides a filtration unit for a sample preparation device, comprising a base part that defines a membrane support, a removable lid for defining a membrane chamber with the base part and sealing the membrane chamber from the environment, and at least one inlet port and at least one outlet port respectively accessible from outside of the filtration unit and communicating with the membrane chamber at positions upstream and downstream of a membrane when the same is provided on the membrane support. The membrane may be part of the filtration unit when the unit is distributed or may be added later. The inlet and outlet port(s) are respectively provided with a sealing mechanism formed so as to be opened upon connection with a mating connector on an external receptacle and so as to be automatically re-sealable upon disconnection.

The provision of the sealing mechanism at the inlet and outlet ports facilitates the handling of the filtration units because the ports are automatically closed once the unit is removed from its receptacle. Further, it renders superfluous the provision of a number of separate external clamps, valves and sealing caps in the sample preparation system because most of these functions are already integrated in the filtration unit. Further, the risk of contamination of the sample in the filter and thus of a false positive detection result is considerably reduced because the sealing mechanisms already upon disconnection of the unit automatically close and seal the internal volumes from the atmosphere and thus avoid the risk of external contamination.

A preferred embodiment of the sealing mechanism is in the form of a septum with a pre-formed opening that is adapted to be pierced by a needle-like connector on the side of the receptacle into which the filter unit is to be inserted and received and which automatically seals the opening due to the resiliency of the material when the connector is withdrawn.

The membrane support comprises a drainage channel arrangement, preferably in the form of a spiral or labyrinth or maze, or a porous support on a cavity, preferably a fritted support, wherein at least one of the ports communicates with the volume of the drainage channel arrangement or cavity. These structures provide for a uniform growth probability because the nutriments supplied through the ports are accessible to the overall or at least substantial membrane surface so that the entire drainage surface can be saturated with the nutrient medium without air bubbles being present, and they avoid or at least considerably limit membrane deformation during operation and local stress and thus potential damage due to the even and direct support of the membrane throughout its surface area. The increased quantity of media adapted to be held below the membrane in case of providing the cavity in combination with the porous support reduces the potential effect of dehydration during incubation of the filtration unit and allows continuous bacterial feeding through the porosity of the support.

The filtration unit having the porous support on a cavity preferably comprises an inlet port and an outlet port communicating with the cavity below the porous support, wherein the opening of the outlet port to the cavity is located closer to the porous support and vertically above the opening of the inlet port to the cavity when the filtration unit is in an upright posture in which the porous support is in a substantially horizontal orientation. This secures that any air bubble trapped under the membrane can be avoided.

Preferably the lid is at least partly, preferably completely transparent to detection means to allow optical and/or physical inspection of a membrane on the membrane support through the lid. Thus, the visual bacterial growth detection (i.e. colony enumeration) can be directly and quickly performed (by the human eye or optical systems and image/pattern detection) at the surface of the membrane without opening the filtration device and breaking the sterility. Simultaneously, the possibility of opening the lid allows easy access to the membrane for further identification.

In a preferred embodiment the base part includes a further cavity or channel that is arranged such that it can be selectively communicated with the membrane chamber, preferably by partly disconnecting the lid from the base part while the membrane chamber remains sealed from the environment. This further cavity can thus contain additional substances that should be selectively brought in communication with the atmosphere in the membrane chamber without breaking the sterility by completely opening the filtration unit and exposing the membrane to the atmosphere, i.e. where particular environmental conditions should be created for the growth of the micro-organisms on the filter. This embodiment is particularly useful for micro-organisms that require an anaerobic environment and in this case the further cavity is sealed by a gas-permeable membrane to allow only gas exchange and/or is pre-filled with an anaerobic generator powder. During the sample preparation steps the further cavity and the gas-permeable membrane that closes it are completely closed by the lid and blocked from communication with the membrane chamber, i.e. by the provision of a separate fluid tight seal at the lid. Just before transferring the filtration unit into the incubator the lid is slightly opened, i.e. by unscrewing it for a limited angle range. Thereby a gap is created between the gas permeable membrane and the membrane chamber that allows the initiation of a reaction between oxygen present in the membrane chamber and the reactive generator powder in the further chamber through the gas permeable membrane while the lid still prevents any contamination from the outside.

For a case where the filtration unit is to be placed in an anaerobic jar during incubation, the base part may have a calibrated vent that is arranged such that it can be selectively communicated with the membrane chamber, again preferably by partly disconnecting the lid from the base part as described above, allowing control air exchange between the membrane chamber and the external environment. The calibrated vent may also be sealed by a gas permeable membrane as described above in connection with the further cavity for anaerobic generator powder to avoid contamination risks.

In the filtration unit the ports are arranged at a bottom of the base part and are surrounded by a peripheral collar protruding beyond the ports. The lid is provided to close a top of the base part. The arrangement of the ports at the bottom and of the lid at the top allows unobstructed visibility of the membrane through the lid and easy removal of and access to the membrane in the membrane chamber when the lid is removed. The arrangement of all ports at the bottom and the fact that the ports are surrounded by the protruding collar protects the ports and the sealing mechanisms from damage and inadvertent opening, especially after the sealing mechanisms thereof have been opened once, i.e. by piercing, and re-sealed during handling after removal of the filtration unit from the receptacle, i.e. for stacking in the incubator or visual inspection.

The filtration unit is preferably formed with an engagement feature at the lid and/or the base such that plural filtration units can be stacked one on top of another, i.e. in the incubator, and prevented from lateral movement. This feature also allows positional fixation and orientation during automated mechanical handling of the filtration units, i.e. during visual inspection.

The present invention also specifically provides a sample preparation device, preferably for sterility testing, comprising a manifold including one or more receptacles for filtration units, preferably the ones of the invention as disclosed in this application, and at least one inlet and/or outlet port. The receptacle(s) is/are respectively provided with at least two connectors for establishing a fluid connection with mating ports of the filtration units upon insertion of the same into the respective receptacles. The connectors are in fluid communication with these inlet and outlet port(s) via channels defined in the manifold to allow a desired fluid transfer through the manifold.

The integration of the receptacles with the connectors and the internal communication channels in the manifold reduces the number of elements required to set-up a sample preparation system and thus considerably accelerates the sterility testing process and reduces the amount of waste due to the integration. It also increases the sample preparation reliability in that it reduces the number of steps and thus the possible errors on the side of an operator to set-up the system and carry out the various steps described further below in this application and it reduces the number of incidents where the sterility of the system could be potentially impaired.

Preferably, the manifold of the sample preparation device further integrally includes one or more receptacles for containers/vials for media and/or reagents, wherein the receptacle(s) for such containers/vials is/are respectively provided with at least one connector for establishing a fluid connection with a mating port of the containers/vials upon insertion of the same into the respective receptacle(s).

The connector(s) is/are in fluid communication with the connectors of the receptacles for the filtration unit(s) via channels defined in the manifold to allow a desired fluid transfer through the manifold. This aspect even further increases the level of integration and reduces the number of steps for carrying out the sterility testing procedures and thus reduces the volume and mass of waste.

The sample preparation device may comprise a common inlet port with a connector, preferably for connection with an external tubing, that is in fluid communication with first connectors of plural receptacles for the filtration units trough split channels, and at least one outlet port with a connector, preferably for connection with an external tubing, that is in fluid communication with second connectors of the plural receptacles for the filtration units trough split channels. With this structure aliquots of the various solutions can be simultaneously directed through the plural filtration units which considerably accelerates the testing process and guarantees that differences in handling that might influence the comparability of the test results are avoided.

The sample preparation device preferably comprises at least one sterile vent filter integrated into the manifold and communicating with at least one of the channels in the manifold, and/or it may comprise one or more deformable or actionable zone(s) which are integrated into the manifold to allow selective actuation from outside. These deformable or actionable zone(s) may be implemented as valve section(s) which allow selective opening/closing of communication through respective channels in the manifold by external actuation or may be implemented as a pump to generate liquid transfer in respective channels. The latter embodiment integrates part of the pumping system into the sample preparation device, i.e. parts of a peristaltic-type pumping system. Similar to the above aspects these features increase the level of integration with the benefit of reducing waste amounts and increasing process reliability and efficiency.

In order to mate with the sealing mechanisms of the filtration units of the invention having a pre-formed opening and automatic re-sealing properties, the connectors of the receptacles are in the form of a hollow needle to allow penetration of these sealing mechanisms of the mating ports of the filtration units or media containers/vials.

The manifold is preferably made from a molded base, preferably of suitable plastics materials to support the disposability of the device, in which molded base the receptacle(s), channels, connectors, vent(s) and/or deformable or actionable zone(s) are integrally formed, and wherein the channels are at least partly formed as open recesses that are closed to the environment and sealed from each other by a bottom plate, cover or film sealingly connected with the base. Since the base and the bottom plate are formed as separate parts that are sealingly combined, the structure of the base with the channels can be simplified and the manufacturing cost, especially due to a reduction of the mold's complexity, can be reduced. Also, if different materials are used for certain elements or parts of the device, the device can be more easily taken apart and separated into these materials and elements which facilitates a recycling of the materials after use The advantages of the above described sample preparation device and filtration unit can be combined in a sample preparation system, preferably for sterility testing, which comprises both entities adapted to match and functionally cooperate with each other. The entire system may be distributed in a package in a pre-sterilized condition.

BRIEF DESCRIPTION OF DRAWINGS

These and other aspects will become apparent from the description of a preferred embodiment described below in connection with the attached drawing. In this drawing:

FIG. 4 is a partially cut-away perspective view of the embodiment of FIG. 1 in an exploded representation;

FIG. 5A-shows a partial detail of an engagement situation between the lid and the base of the embodiment of the filtration unit of FIG. 1 in one position;

FIG. 5B-shows a partial detail of an engagement situation between the lid and the base of the embodiment of the filtration unit of FIG. 1 in another position;

FIG. 8 is a partially cut-away perspective view of the sample preparation device with the media container and filtration unit not yet completely engaged with the connectors;

FIG. 9 is a similar view as FIG. 8 but with the media container and filtration unit completely engaged with the connectors;

FIG. 13B-shows a typical step of a sterility testing procedure using the filtration unit of the present invention in a diagrammatic representation.

FIG. 13C-shows a typical step of a sterility testing procedure using the filtration unit of the present invention in a diagrammatic representation.

Figure 1:
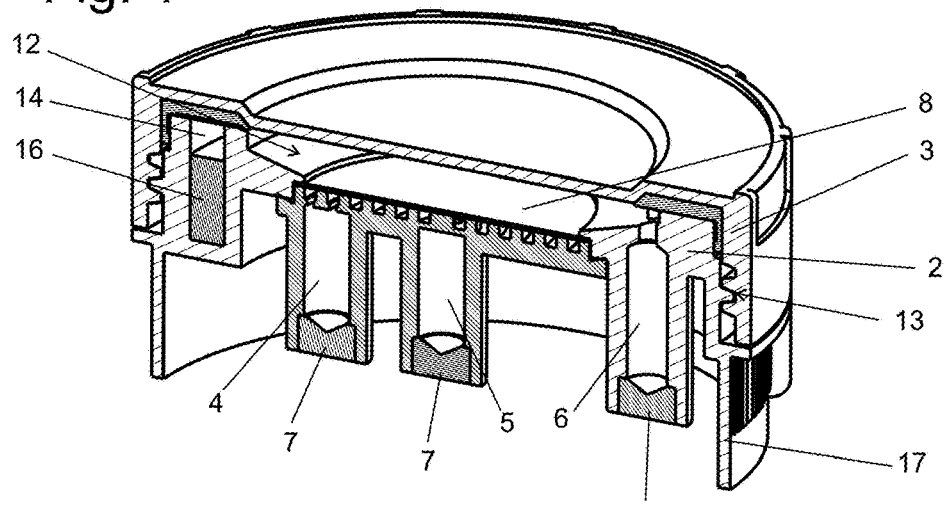
FIG. 1 is a partially cut-away perspective view of filtration unit according to an embodiment of the invention.

The filtration unit for a sample preparation device according to a first embodiment of the present invention is shown in FIG. 1, 2, 4, 5a, 5b and FIG. 6. The filtration unit comprises a base part 2 that defines a membrane support 9 for supporting a membrane 8. The membrane 8 can be integrated into the filtration unit as sold or can be subsequently placed on the support. For this purpose the filtration unit comprises a removable lid 3 which, together with the base part 2 defines a membrane chamber 12 and seals the membrane chamber 12 from the environment when the lid 3 is attached to the base part 2, for example, by means of the threaded connection 13. Alternative connections like bayonet-type connections or friction-type connections are possible.

In order to reliably seal the membrane chamber 12 from the environment, a seal or gasket 19 with a peripheral seal lip 19a is provided at the lid 3 as shown, for example, in FIGS. 4 and 5a and 5b. The peripheral seal lip 19a is dimensioned and arranged such that it allows partial disconnection of the lid 3 from the base part 2 while the sealing condition of the membrane chamber 12 with respect to the environment is maintained. This aspect is particularly useful if the base part includes a further cavity 14 or channel that can be, for example, arranged in the thicker peripheral rim of the base part as shown in FIGS. 1 to 5 and which may hold an anaerobic generator powder 16 or provide a communication and anaerobic exchange with a vial or an external gas generator. The further cavity 14 or channel may thus be selectively communicated with the membrane chamber 12 by partially disconnecting the lid from the base part as is indicated in FIGS. 5a and 5b. The further cavity may be sealed at its top opening by a gas-permeable but membrane 15 so as to retain the powder 16 in the cavity and allow communication of gasses through the membrane between the further cavity 14 and the membrane chamber 12 through a gap in the vicinity of the seal 19 that is created when the lid is partially separated from its sealing seat on the base part (see FIG. 5b). If a threaded connection 13 between the lid and the base part is provided such partial opening may be obtained in that the lid is slightly unscrewed by a certain angle range (30° for example). The anaerobic generator powder 16 that may be placed in the further cavity could be, for example, "Gen bag anaer" from Biomerieux erf 96124. The path through the gap for gas exchange is symbolized by the arrow in FIG. 5b. The connection between the cavity 14 and the chamber 12 may be established during incubation steps whereas the further cavity with the anaerobic generator powder is completely sealed from the membrane chamber during filtration steps as shown in FIG. 5a.

Figure 2:
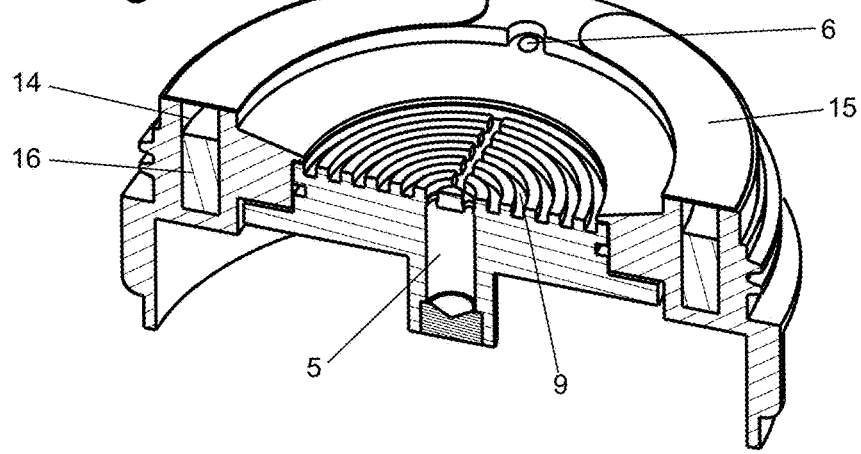
FIG. 2 is another partially cut-away perspective view of the embodiment of FIG. 1 from a different direction and with the lid removed.

In the embodiment of the filtration unit shown in FIGS. 1 and 2 the membrane support 9 includes a drainage structure with a pattern of ribs or convex protrusions defining drainage channels distributed substantially over the entire surface of the support. These channels may be formed like a spiral or in any other labyrinth or maze design as is known in the art in principle. This aspect provides the effect that a liquid medium introduced into the membrane chamber through the inlet port 6 upstream of the membrane or through the further inlet 4 downstream of the membrane is evenly distributed or collected below the membrane placed on the support and is guided towards the outlet port 5 in the center of the support.

Figure 3:
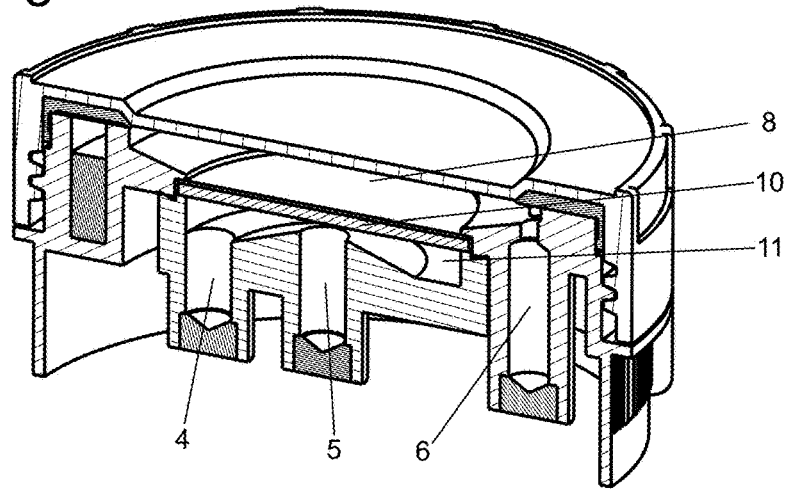
FIG. 3 is a partially cut-away perspective view of an alternative embodiment of the filtration unit of the present invention.

In an alternative embodiment shown in FIG. 3 the support for the membrane may alternatively be formed by a porous support plate 10, i.e. in the form of a fritted support, and a larger cavity 11 for media or staining agents located directly below the porous support plate 10. The larger volume of the cavity 11 may hold a larger amount of media which may be beneficial if potential effects of dehydration during incubation should be reduced and continuous bacterial feeding through the porosity of the fritted of porous support plate should be allowed. This larger media cavity below the porous support plate can be formed with a central elevation, preferably in a slightly conical form as shown in FIG. 3, so that the opening of the outlet 5 into the cavity is located at a higher position than the opening of the inlet 4 into cavity that is located at the peripheral edge so that the opening of the outlet port is effectively located closer to the porous support and vertically above the opening of the inlet port when the filtration unit is in an operating posture in which the porous support is in a substantially horizontal orientation. This design provides the effect that air bubbles are forcibly eliminated during the media transfer.

The membrane chamber 12 can have a peripheral wall 18 that is conical and inclined from the outer periphery towards the more central membrane support as shown in FIG. 2 or 4. The wall surface may be additionally provided with hydrophobic properties in order to avoid any remaining droplet in the upper chamber after filtration (which will be described in connection with the use of the filtration unit in sterility testing later).

The lid 3 of the filtration unit 1 as shown in the embodiments is completely made from a material transparent to detection means to allow optical and/or physical inspection of a membrane placed on the membrane support during the later described reading steps of the sterility testing process, for example. The reading may be performed by the naked eye or through optical detection systems like cameras and digital image analysis. It is not required that the entire lid is made from a transparent material but it is useful that the lid is at least partly transparent, at least at the top portion opposed to the membrane support, i.e. by providing a transparent window in an otherwise opaque lid material.

The form of the lid is such that a distance between the transparent portion opposite to the membrane support and the membrane on the support is minimized. The transparency of the lid or of the window in the lid is selected such that it allows optical detection with an angle preferably between −45° to +45°. The lid or window material and optional surface treatment are selected to avoid any detection signal perturbation (for example securing low material fluorescence, low luminescence, very high transparency, no mist formation due to temperature change, no diffraction effect). The optical surface may be for example modified or coated with an anti-fog treatment to avoid mist formation when the filtration unit is moved from one incubation temperature area to one different reading temperature area.

The base part 2 of the filtration unit is moreover provided with at least one inlet port 4 or 6 and at least one outlet port 5. The inlet and outlet ports may be selectively provided and used depending on the process steps to be performed. The inlet port 4 and the outlet port 5 open to the volume of the membrane chamber below or downstream of the membrane 8, i.e. to the volume of the spiral or labyrinth channels of the drainage channel arrangement 9 or the cavity 11 below the porous support plate 10 as shown in FIGS. 1 and 3.

Each of the inlet and outlet ports 4, 5 and 6 is provided with a sealing mechanism 7 that is of a structure that allows it to be opened upon connection with a mating connector (to be described later) on an external receptacle and so as to be automatically re-sealable upon disconnection from the connector. A typical structure for such sealing mechanism is a septum with a pre-formed opening that is adapted to be pierced by a needle-like connector and that is further adapted to automatically close the opening due to its resiliency once the connector is withdrawn. The sealing mechanism can be therefore formed from a rubber-like material that can be inserted into the outer end of the respective inlet and outlet ports after molding or that can be insert-molded into a corresponding recess during the molding process. The material chosen for the sealing element of the sealing mechanism is typically different from the plastic material used for forming the base part. Other sealing mechanisms like valve elements which are known in the art may be used as well provided they fulfill the function of selective opening and automatic sealing when the inlet/outlet ports are disconnected from the respective connectors. The number of inlet and outlet ports is not limited to one and ports can be placed anywhere below the membrane support to maximize the performance in terms of flow and efficiency.

The inlet and outlet ports are all arranged at the bottom of the base part 2 and are surrounded by a peripheral collar 17 protruding beyond the lower end of the ports. The peripheral collar 17 serves to protect the ports and especially the sealing mechanisms from inadvertent opening, especially after the sealing mechanisms have been opened once and re-sealed when the filtration unit is disconnected from the connectors for further processing. Another effect of the collar is to guide the insertion of the filtration unit into the respective receptacles of a sample preparation device as is, for example, shown in FIGS. 8 and 9 to be described later. The peripheral collar 17 may be replaced by a number of discontinuous protrusions located about the periphery of the base part provided they fulfill the above function. An annular seal (not shown) may be provided to secure fluid tightness between the collar and the respective receptacle.

Figure 6:
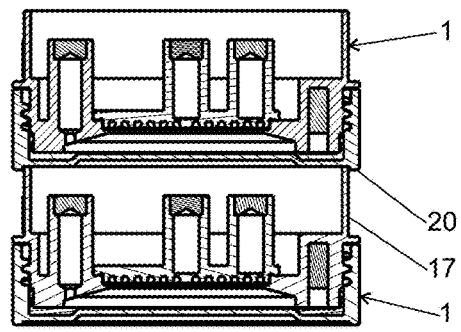
FIG. 6 shows the embodiment of FIG. 1 in an inverted stacked state and in a partial cut-away front view.

As shown in FIG. 6 the filtration unit is formed with an engagement feature 20, for example, in the form of a peripheral protrusion or rim, either continuous or in the form of plural protrusions distributed about the circumference of the lid and arranged such that plural filtration units of the same type can be stacked one on top of another and prevented from lateral movement. Preferably the peripheral collars 17 or discontinuous protrusions at the bottom side of the base parts cooperate with the engagement feature 20 at the top side of the lid so that the plural filtration units can be stacked in regular posture or upside down as shown in FIG. 6. An embodiment where plural protrusions serving as engagement feature are provided and evenly distributed about the peripheral edge of the upper part of the lid is shown in FIG. 4.

The material for the membrane (8) placed on the membrane support 9 or 10 is not particularly critical for the filtration unit and maybe chosen according to the intended testing purpose. A micro-porous membrane is frequently used for sterility and bioburden testing which is the most preferred field of application of the present invention.

The invention also concerns a sample preparation device which is designed to cooperate with the filtration unit of the invention described before. An example of such a sample preparation device is shown in FIGS. 7 to 12 and the details thereof are described below.

Figure 7:
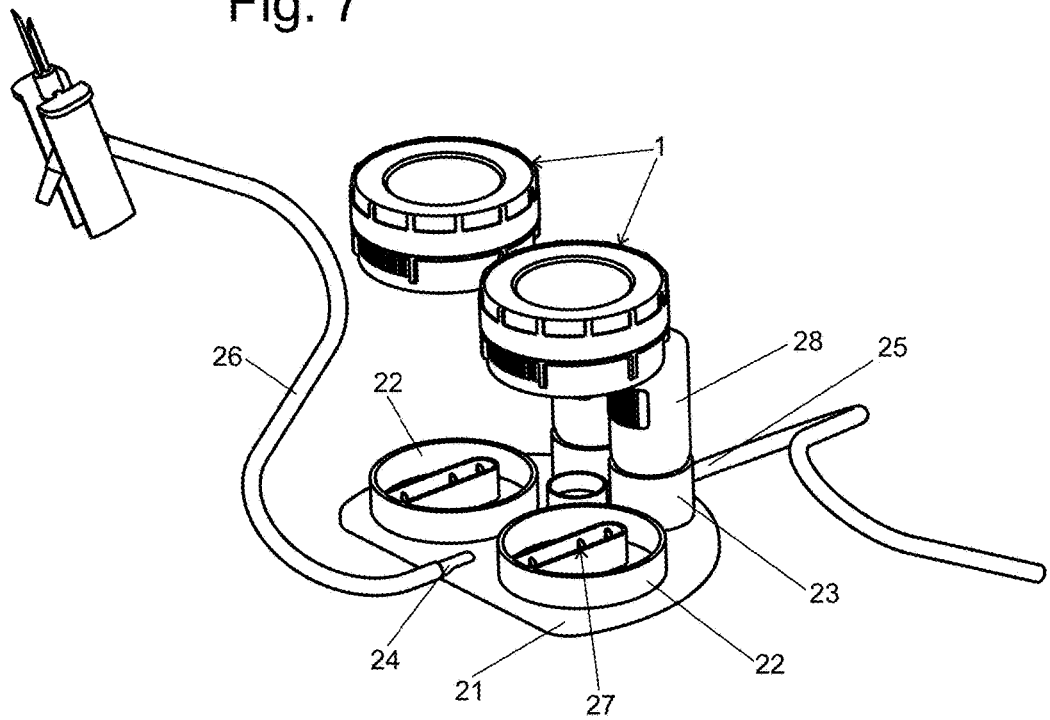
FIG. 7 is an exploded perspective view of sample preparation device of the invention with filtration units in a separated state.

In the most general layout the sample preparation device comprises a manifold 21 including one or more receptacles 22 for filtration units 1 and at least one inlet port 24 and/or at least one outlet port 25 (see FIG. 7). The receptacles are respectively provided with at least two connectors 27 for establishing a fluid connection with mating ports of the filtration units upon insertion of the filtration units into the respective receptacles. The connectors 27 of the receptacles 22 are preferably in the form of a hollow needle that allows penetration of the sealing mechanisms of the ports of the filtration units and provides a fluid communication with the ports once the connection is established. The shape of the connectors 27 is as such not critical as long as the releasable connection with the sealing mechanisms of the ports and the automatic re-sealing of these sealing mechanisms after disconnection is achieved. A typical example is a hollow needle with a pointed or rounded tip placed to pierce a pre-formed opening in the sealing mechanism in the form of a septum, seal element or gasket. As long as the connection is established, the resiliency of the seal mechanism seals about the circumference of the needle and the resiliency is chosen such that upon withdrawal of the needle from the sealing mechanism the opening is closed. The number and location of the connectors in the receptacles is accordingly chosen to match the location and number of the ports of the filtration units intended to be used with the sample preparation device.

The receptacles 22 are furthermore formed with an engaging feature in the form of a peripheral wall, for example, that cooperates with the peripheral collar 17 of the filtration units to guide the insertion and disconnection of the filtration units from the receptacles. It may also be provided with features enforcing a proper alignment during the insertion process, i.e. in the form of a key or other means known in the art that mechanically prevent insertion of a filtration unit in an incorrect orientation, and an annular seal (not shown) as mentioned above in addition or as an alternative to the annular seal of the filtration unit to secure fluid tightness between the collar and the receptacle.

The connectors 27 of the receptacles 22 of the manifold 21 are in fluid in communication with the inlet and outlet ports 24, 24 via various channels formed in the manifold to allow a desired fluid transfer through the manifold.

In a further preferred modification the manifold may additionally include one or more further receptacles 23 for containers/vials for media and/or reagents and these receptacles 23 are provided with at least one connector for establishing a fluid connection with a mating port of the media/reagent containers/vials upon insertion of the same into the respective receptacles 23 as described above in connection with the filtration unit. Accordingly, the connectors 27 of these receptacles 23 may be formed similar to those of the filtration units but may be also formed differently depending on the sealing mechanism and connecting counter part of the containers/vials to be received in the receptacles. The receptacles 23 likewise can be formed so as to guide and hold the containers/vials during the insertion process and may accordingly be adapted to match the respective container type and form and they may be provided with an annular seal. Here, too, mechanical means can be provided to prevent insertion of incorrect containers or of correct containers in wrong orientation. The connectors 27 of the receptacles 23 for the media containers/vials are also in fluid communication with the connectors of the receptacles for the filtration units via channels defined in the manifold to allow the desired fluid transfer through the manifold and between the containers/vials and filtration units.

Figure 10:
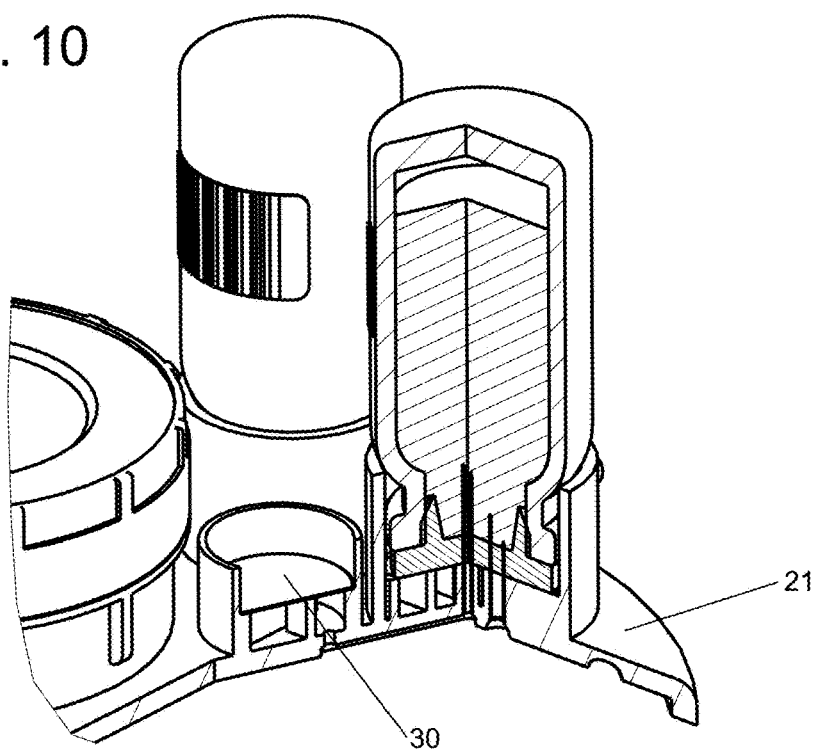
FIG. 10 is a partially cut-away view of the detail of the sample preparation device including the media container and a vent filter integrated into the manifold of the sample preparation device.
Figure 11:
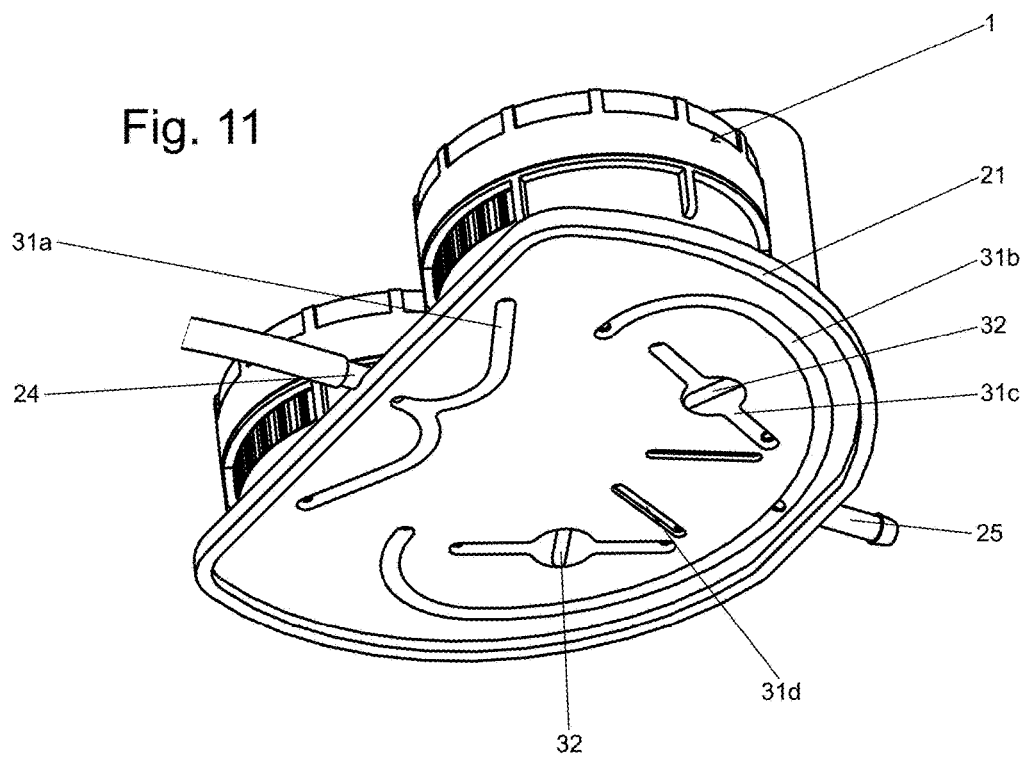
FIG. 11 is a perspective view seen from the bottom of the sample preparation device with the bottom plate removed to show details of the channels defined in the manifold.

As shown in FIG. 10 the manifold 21 may optionally include an integral vent filter 10 that communicates with the channels 31d of the manifold to allow venting of the media or other liquids in the containers/vials in order to allow continuous media transfer (see FIG. 11).

The inlet and outlet ports 24 and 25 of the manifold may be provided with needles or disposable connectors, for example in the form of a luer connector or a more sophisticated quick connector with or without a valve to shut off the pathway in disconnected position and avoid waste spill. They may also be provided with a breakaway coupling (not shown).

Figure 12:
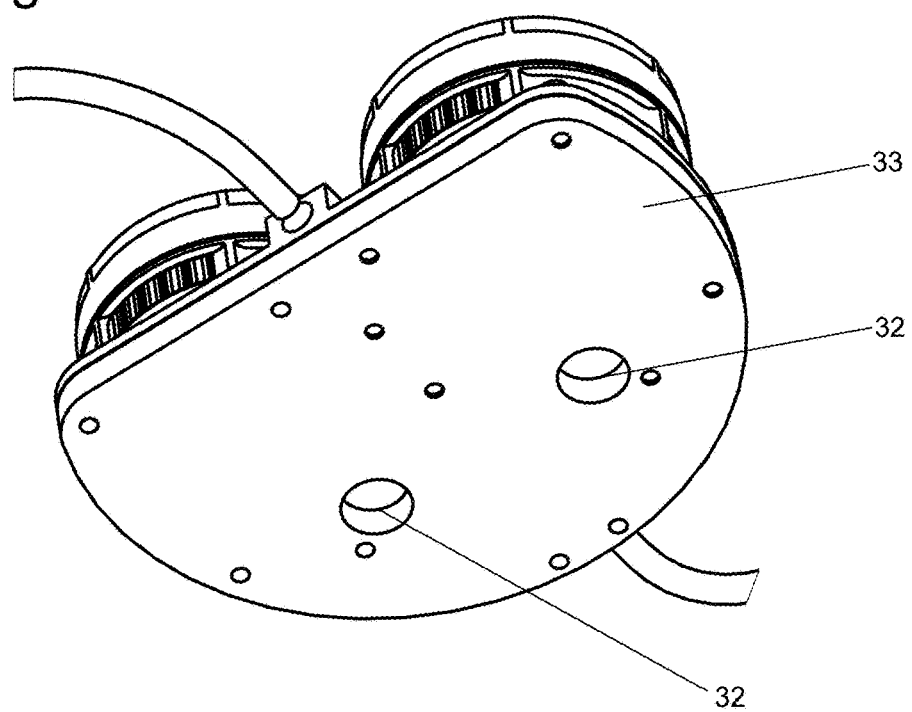
FIG. 12 is a similar view as FIG. 11 with the bottom plate attached.

In a preferred embodiment the sample preparation device as shown in FIGS. 7 and 11 and 12 has a common inlet port 24 with a connector preferable for a releasable connection with an external tubing, that is in fluid communication with first connectors of a pair of receptacles 22 for the filtration units 1 through split channels 31a and with an common outlet port 25 with a releasable connector, again preferably for connection with an external tubing, that is in fluid communication with second connectors 27 of the receptacles 22 for the filtration units 1 through split channels 31b. The provision of such split channels allows flowing of aliquots of the respective solutions into the manifold or from the manifold to a drain. At least for the outlet port separate outlet ports may be used instead of a common outlet port. The channels may be designed in cross-section, length and roughness to optimize the equal splitting of the fluid.

The manifold additionally comprises channels 31c that connect the connector 27 of the receptacles 23 for the media containers/vials with a further connector of the respective receptacle 22 of the filtration units 1. These channels 31c are each provided with a valve section 32, preferably in the form of a deformable or actionable zone forming a pinch valve, which is integrated into the manifold to allow a selective opening/closing of these channels in the manifold by external actuation. The mechanical actuator may access the valve sections from the bottom of the manifold through a window in a bottom plate 33 as shown in FIG. 12. These deformable or actionable zones may also be formed and used as part of a pumping system, i.e. a peristaltic-type pumping system, to generate the liquid transfer in the channels.

In an alternative arrangement the split channels for the inlet port and/or the outlet port may be omitted in the manifold and embodied in the external tubing. In this case the manifold has a pair of inlet and or outlet ports. An advantage of this modification is that the solutions may be supplied into or from the respective filtration units independently at different rates using separate external pumps or pump heads.

The manifold is made from a molded base in which the receptacles, the channels, the connectors, the vents and/or the valve sections are integrally formed and wherein the channels are at least partly formed as opened recesses that are closed to the environment and are sealed from each other by a separate bottom plate, cover or film 33 sealingly connected with the base. The FIG. 11 shows the base without the bottom plate whereas the FIG. 12 shows the manifold with the bottom plate in base. The manifold and the filtration units maybe formed from any material selected such that these components may be discarded after use. The selection of materials is accordingly not critical as long as the materials are suited for the purpose and can withstand chemical solutions intended to be processed and sterilization, as long as they allow the molding or forming to the desired shape, and as long as they allow disposing or recycling when this is intended.

To provide maximum sterility and efficiency the sample preparation device described above is preferably designed to be disposable, and one or more filtration units of the invention that are adapted to be removably fitted into the receptacles of the manifold of the sample preparation device, i.e. that are provided with mating ports for the connectors, are combined to form a sample preparation system that is pre-sterilized and packaged as a unit. Even the appropriate media/reagent containers/vials can be included in the system and pre-arranged for insertion into the respective receptacles as shown, for example in FIG. 8, without establishing the fluid connection between the connectors and the ports yet. At the point of use the system may be taken out from the package and connected with the inlet and outlet ports to external tubing that may cooperate with external fluid containers and pumps or customer samples (vials, bottles, bags, etc.), preferable as described below in connection with the sequence of FIG. 13A to G to carry out a typical sterility testing procedure. In addition or as an alternative to packaging in a bag or the like, the receptacles for filtration units, the receptacles for media/reagent containers/vial and the vent can be individually or globally closed by a removable seal to assure integrity before use and to serve as a warrantee for a first use and clean surfaces.

To allow traceability and identification the filtration units and the media or reagent containers/vials can be provided with unique identification tags, i.e. in the form of a bar code, data matrix, RFID tag etc, which can be read either with a manual scan or a scan integrated into any process instrument. This aspect supports easy recording and tracking of processed samples and consumables, media, rinsing fluids and association to a particular test.

The following is a description of a typical sample preparation process for sterility testing using the device of the present invention. Although the schematic representation shows the use of a single filter unit and of a single nutriment medium container only and does not depict the manifold as such, the actually used manifold preferably has two or three or even more receptacles and consequently a corresponding number of filter units and nutriment medium containers C removably inserted into the respective receptacles.

The system is set-up by placing the filter units in the receptacles of the manifold of the sample preparation device and connecting the rinsing buffer container A with the inlet port via a first pump P1, which is preferably an external peristaltic type pump engaging with a flexible tubing leading from the rinsing buffer container to the inlet port. A second external pump P2 is provided which is preferably also a peristaltic type pump engaging with a flexible tubing leading from the outlet port to a waste drain or collection container. Nutriment media containers (i.e. aerobic and anaerobic) are also placed in the respective receptacles but remain disconnected from communication with the respective filtration units in that the valve sections in the communication channels of the manifold remain closed.

Alternatively, the nutrient media containers may be arranged in the receptacles at a first position where the connectors have not yet entered and opened the sealing mechanisms in the ports of the containers or vials. The connection and communication with the channels in the manifold may be selectively established by fully pushing the containers into the receptacles upon which the connectors are opening the sealing mechanisms.

In the following description the starting and stopping of the pumps P1 and P2 is generally described. The starting and stopping and the duration of operation as well as the opening and closing of any valve mechanisms can, however, be either controlled manually or, more preferably, by an automated process using known control devices (dedicated pre-programmed logic circuitry or programmable universal computers with dedicated software) and electrical remote operation and activation of the pumps and valve mechanisms.

Figure 13A:
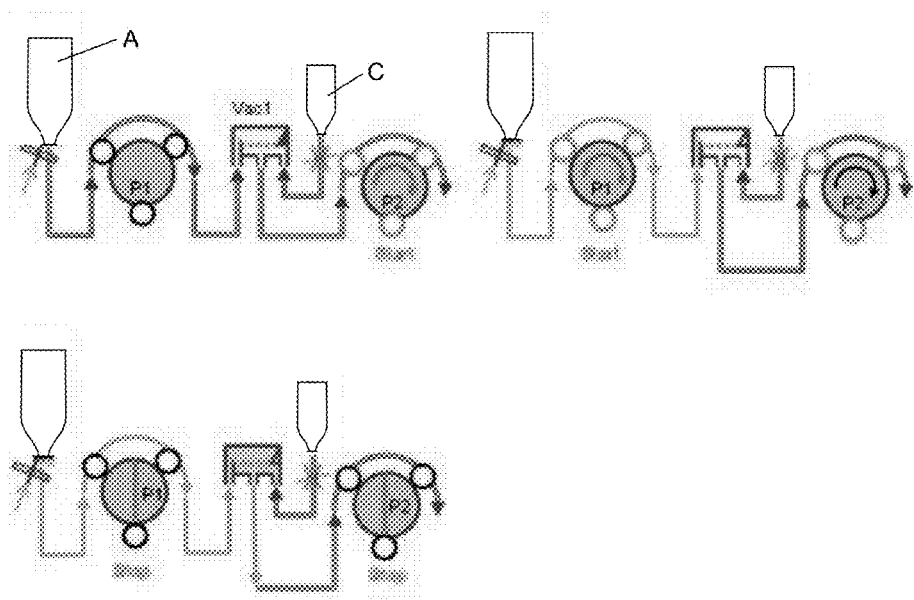
FIG. 13A-shows a typical step of a sterility testing procedure using the filtration unit of the present invention in a diagrammatic representation.

Pre Wetting (FIG. 13A)

With these steps the porosity of the membrane of the filter units is saturated with the proper rinsing buffer in order to avoid or at least reduce the risk of molecule binding to the membrane (mostly in case of antibiotic sterility testing).

The pump P2 is started first to create a certain vacuum in the filtration units. After a few seconds the pump P1 is started, too, to transfer the rinsing agent until the membrane chambers of the filtration units are completely filled. At this time the two pumps P1 and P2 are stopped.

Sample Filtration (FIG. 13B)

With these steps the micro-organisms are concentrated on the surface of the membrane.

The rinsing buffer container A is disconnected and replaced by a sample solution container B. Both pumps P1 and P2 are simultaneously started and operated until the rinsing agent is expelled and a pre-determined sample volume has been split and transferred through the number of filtration units of the manifold.

Rinsing (FIG. 13C)

With these steps all the tubing set and the internal walls of the filter units are rinsed to be sure that all the micro-organisms are collected at the surface of the membranes. Further, the porosity of the membranes is rinsed in order to remove any inhibitor which may delay or prevent growth development of potential contaminants.

The sample solution container B is disconnected and replaced by a rinsing buffer container A. Both pumps P1 and P2 are simultaneously started and operated until the pre-determined rinsing volume has been split and transferred through the number of filtration units of the manifold. This can be done several times with the same or different rinsing agent. Then, the rinsing buffer container A is flipped back to purge the inlet tubing and the upper side of the membrane chamber of the filtration units (above or upstream of the membrane). For this operation either both pumps P1 and P2 or only the pump P2 can be operated. Then the pump(s) previously operated is/are stopped.

Figure 13D:
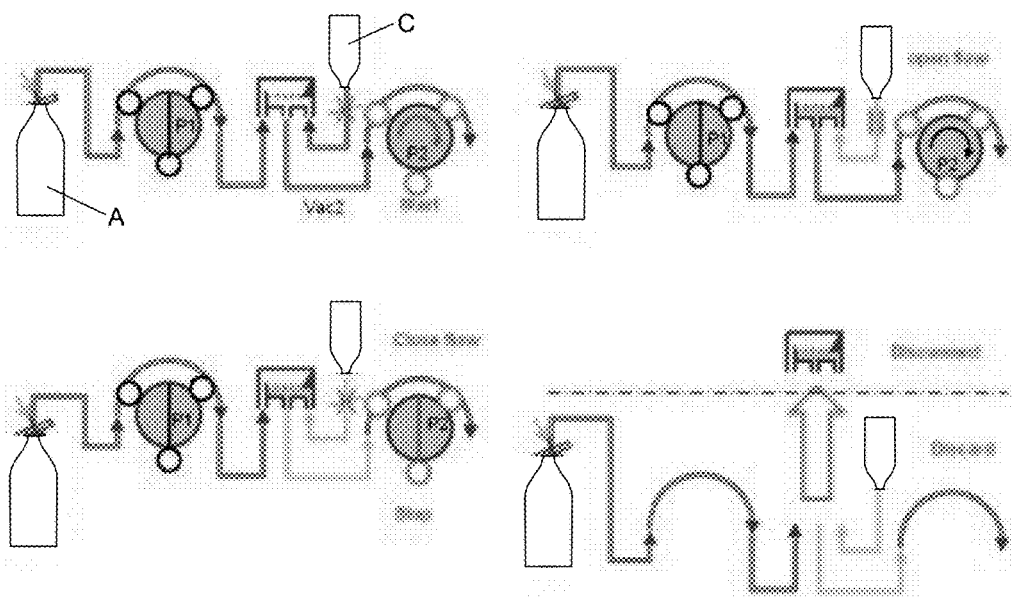
FIG. 13D-shows a typical step of a sterility testing procedure using the filtration unit of the present invention in a diagrammatic representation.

Addition of Media and/or Reagents (FIG. 13D)

With these steps the proper volume of selected media and/or reagents like nutriments (aerobic or anaerobic) are brought into the membrane chamber of each of the filtration units (under or downstream of the membrane).

The pump P2 is operated to create a certain vacuum in each of the filtrations units under or upstream of the membrane (the membranes can be considered as fully tight due to the air bubble intrusion pressure level). The valve sections of the manifold (i.e. the deformable zones forming pinch valves) are then opened (simultaneously or not) on each of the media channels (aerobic and anaerobic). When the two nutriment media from the respective containers C have filled the membrane chamber of each of the filtration units (under or downstream of the membrane), the pump P2 is stopped and the valve sections of the manifold are closed. The filtration units can then be disconnected from their receptacles (causing the automatic sealing of the ports) and transferred to respective incubators. The sample preparation device (i.e. the manifold and external tubing) is discarded if it is of a disposable design.

Figure 13E:
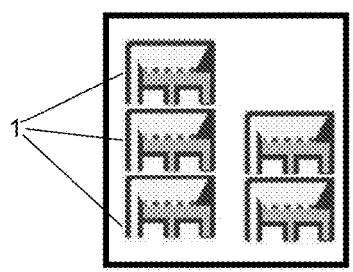
FIG. 13E-shows a typical step of a sterility testing procedure using the filtration unit of the present invention in a diagrammatic representation.

Incubation (FIG. 13E)

The filtration units are incubated in their respective specific incubation conditions for yeast and mold and optimal bacterial growth development. Due to the engagement feature several filtration units can be reliably stacked one upon the other upright or upside down in order to minimize the footprint required inside the incubators.

Figure 13F:
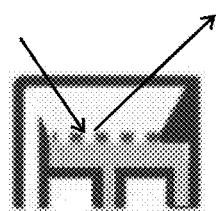
FIG. 13F-shows a typical step of a sterility testing procedure using the filtration unit of the present invention in a diagrammatic representation.

Reading (FIG. 13F)

After the incubation is completed any microorganism growth can be detected at the surface of the membrane.

This reading is regularly performed by naked eye inspection through the transparent portions of the lid without the need to open the units or by using automatic optical sensitive detection systems.

Figure 13G:
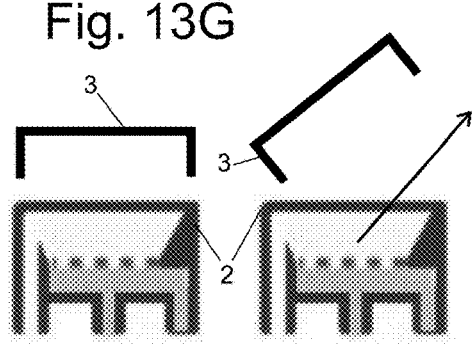
FIG. 13G-shows a typical step of a sterility testing procedure using the filtration unit of the present invention in a diagrammatic representation.

Identification (FIG. 13G)

In case of positive detection, after incubation, the filtration units can be opened if so desired by completely removing the lid from the base, i.e. in an aseptic environment like a laminar flow hood or an isolator, to access the colony for further identification purposes. Micro-organisms forming colonies can be thus easily extracted from the filtration unit, i.e. using standard microbiological methods and devices, for further analysis including identification. The filtration units can then be discarded as well.

The invention claimed is:

1. A filtration unit (1) capable of use in a sample preparation device, said unit comprising
    a base part (2) that defines a membrane support (9;10);
    a removable lid (3) defining a membrane chamber (12) with said base part (2) and sealing the membrane chamber (12) from the environment;
    at least one inlet port (4,6) and at least one outlet port (5) respectively accessible from outside and communicating with said membrane chamber (12) at positions upstream and downstream of a membrane (8) when the same is provided on said membrane support (9;10),
    wherein said inlet and outlet port(s) (4,5,6) are respectively provided with a sealing mechanism (7) formed so as to be opened upon connection with a mating connector on an external receptacle and so as to be automatically re-sealable upon disconnection.

2. The filtration unit (1) according to claim 1, wherein the sealing mechanism (7) is in the form of a septum with a pre-formed opening adapted to be pierced by a needle-like connector.

3. The filtration unit (1) according to claim 1, wherein the membrane support comprises a drainage channel arrangement (9), or a porous support (10) on a cavity (11), wherein at least one of the ports (4,5) communicates with the volume of the drainage channel arrangement (9) or cavity (10).

4. The filtration unit (1) according to claim 3, comprising an inlet port (4) and an outlet port (5) communicating with said cavity (10), wherein the opening of the outlet port (5) to the cavity (11) is located closer to the porous support (10) and vertically above the opening of the inlet port (4) to the cavity (11) when the filtration unit (1) is in an upright posture in which the porous support (10) is in a substantially horizontal orientation.

5. The filtration unit (1) according to claim 1, wherein the lid (3) is at least partly transparent to detection means to allow optical and/or physical inspection of a membrane (8) on the membrane support (9;10).

6. The filtration unit (1) according to claim 1, wherein the base part (2) has a further cavity or channel (14) that is arranged such that it can be selectively communicated with the membrane chamber (12).

7. The filtration unit (1) according to claim 1, wherein the base part (2) has a calibrated vent that is arranged such that it can be selectively communicated with the membrane chamber (12).

8. The filtration unit (1) according to claim 6, wherein the further cavity or channel (14) is sealed by a gas-permeable membrane (15) and/or filled with an anaerobic generator powder (16).

9. The filtration unit (1) according to claim 1, wherein the ports (4,5,6) are arranged at a bottom of the base part (2) and are surrounded by a peripheral collar (17) protruding beyond the ports (4,5,6), and the lid (3) is provided to close a top of the base part (2).

10. A sample preparation device, capable of sterility testing, comprising
    a manifold (21) including one or more receptacles (22) for the filtration units (1) according to the claim 1 and at least one inlet port (24) and/or at least one outlet port (25),
    wherein said receptacle(s) (22) is/are respectively provided with at least two connectors (27) for establishing a fluid connection with mating ports (4,5,6) of the filtration units (1) upon insertion of the same into the respective receptacles (22); and
    wherein said connectors (27) are in fluid communication with said inlet and outlet port(s) (24,25) via channels (31a,31b) defined in the manifold (21) to allow a desired fluid transfer through the manifold (21).

11. The sample preparation device according to claim 10, wherein said manifold (21) further includes one or more receptacle(s) (23) for containers/vials (28) for media and/or reagents,
    wherein said receptacle(s) (23) for containers/vials (28) is/are respectively provided with at least one connector (27) for establishing a fluid connection with a mating port of the containers/vials (28) upon insertion of the same into the respective receptacles (23); and
    wherein said connector(s) (27) is/are in fluid communication with said connectors (27) of said receptacles (22) for the filtration unit(s) (1) via channels (31c) defined in the manifold (21) to allow a desired fluid transfer through the manifold (21).

12. The sample preparation device according to claim 10 further comprising a common inlet port (24) with a connector, optionally in connection with an external tubing, said port (24) in fluid communication with first connectors (27) of plural receptacles (22) for the filtration units (1) trough split channels (31a), and at least one outlet port (25) with a connector, optionally in connection with an external tubing, said port (25) in fluid communication with second connectors (27) of said plural receptacles (22) for the filtration units (1) through channels (31b).

13. The sample preparation device according to claim 10, further comprising at least one sterile vent filter (30) integrated into the manifold (21) and communicating with at least one of the channels in the manifold (21).

14. The sample preparation device according to claim 10, further comprising one or more zone(s) that are actionable or deformable by external operation, to allow selective opening/closing of respective channels in the manifold (21)

and/or a pump to generate a liquid transfer inside respective channels in the manifold (21).

15. The sample preparation device according to claim 10, wherein the connectors (27) of the receptacles (22,23) are in the form of a needle to allow penetration of a sealing mechanism (7) of the mating port (4,5,6) of the filtration unit (1) or container/vial (28) for media and/or reagents.

16. The sample preparation device according to claim 10, wherein the manifold (21) is made from a molded base in which the receptacle(s) (22,23), channels (31a,31b,31c), connectors (27), vent(s) (30), and/or deformable or actionable zone(s) (32) are integrally formed, and wherein the channels (31a,31b,31c) are at least partly formed as open recesses that are closed to the environment and sealed from each other by a bottom plate, cover or film (33) sealingly connected with the base.

17. A sample preparation system, capable of sterility testing, comprising
   a sample preparation device according to claim 10, optionally designed to be disposable, and
   one or more filtration unit(s) (1) adapted to be removably fitted into the receptacle(s) (22) of the manifold (21) of the sample preparation device and thereby establishing a fluid connection between the connectors (27) and mating ports (4,5,6), said unit(s) (1) comprising
   a base part (2) that defines a membrane support (9;10);
   a removable lid (3) for defining a membrane chamber (12) with said base part (2) and sealing the membrane chamber (12) from the environment;
   at least one inlet port (4,6) and at least one outlet port (5) respectively accessible from outside and communicating with said membrane chamber (12) at positions upstream and downstream of a membrane (8) when the same is provided on said membrane support (12),
   wherein said inlet and outlet port(s) (4,5,6) are respectively provided with a sealing mechanism (7) formed so as to be opened upon connection with a mating connector on an external receptacle and so as to be automatically re-sealable upon disconnection.

18. The filtration unit (1) according to claim 1, wherein the drainage channel arrangement (9) is in the form of a spiral or labyrinth or maze.

19. The filtration unit (1) according to claim 1, wherein the porous support (10) is a fritted support.

20. The filtration unit (1) according to claim 6, wherein cavity or channel (14) can be selectively communicated with membrane chamber (12) by partly disconnecting the lid (3) from the base part (2) while the membrane chamber (12) remains sealed from the environment or by partly disconnecting the lid (3) from the base part (2) allowing control air exchange between the membrane chamber (12) and the external environment.

* * * * *